| United States Patent [19] | [11] | 4,284,572 |
|---|---|---|
| Stanley et al. | [45] | Aug. 18, 1981 |

[54] BLOCKED ISOCYANATE DIOLS AND PREPARATION THEREOF

[75] Inventors: Henry Stanley, Cedar Grove; Dilip K. Ray-Chaudhuri, Bridgewater, both of N.J.

[73] Assignee: National Starch and Chemical Corporation, Bridgewater, N.J.

[21] Appl. No.: 969,771

[22] Filed: Dec. 15, 1978

[51] Int. Cl.³ ............... C07D 307/16; C07C 127/19; C07C 69/78

[52] U.S. Cl. ............ 260/347.4; 260/326.45; 260/453 R; 528/45; 528/65; 548/361; 560/27; 560/28; 560/29; 560/125; 560/144; 560/145; 560/159; 564/50; 564/51; 564/59

[58] Field of Search ......... 260/553 A, 553 R, 553 C, 260/453 R, 326.45, 347.4; 548/361; 528/65, 45; 560/28, 125, 144, 145, 159, 27, 29; 564/50, 51, 59

[56] References Cited

U.S. PATENT DOCUMENTS

| 2,568,885 | 9/1951 | Dreyfus ........................ 260/77.5 |
| 2,988,538 | 6/1961 | Thoma et al. ............ 260/553 A X |
| 3,173,896 | 3/1965 | Adams et al. ............ 260/553 A X |
| 3,682,867 | 8/1972 | Shackelford et al. ....... 260/553 A X |
| 3,833,525 | 9/1974 | Orlando et al. ............ 260/2.5 AC |
| 4,153,775 | 5/1979 | Winkelmann et al. ............ 528/45 |
| 4,211,699 | 7/1980 | Winkelmann et al. ...... 260/553 A X |

FOREIGN PATENT DOCUMENTS

| 2536976 | 3/1976 | Fed. Rep. of Germany ...... 260/553 A |
| 45-34708 | 11/1970 | Japan . |
| 50-27057 | 9/1975 | Japan . |

OTHER PUBLICATIONS

Kawaguchi et al., CA 84: 32694e (1976).

*Primary Examiner*—Thomas A. Waltz
*Attorney, Agent, or Firm*—Edwin Szala; Janet E. Hasak

[57] ABSTRACT

Copolymerizable blocked isocyanate diols are prepared by reacting a blocking agent with an isocyanate group of an organic diisocyanate under controlled conditions, thereby forming a blocked isocyanate group, and reacting the second isocyanate group in a subsequent step with the amine portion of a selected amine diol under anhydrous conditions. The resultant products are used to prepare self-crosslinkable, linear polyurethanes of high molecular weight.

7 Claims, No Drawings

BLOCKED ISOCYANATE DIOLS AND PREPARATION THEREOF

BACKGROUND OF THE INVENTION

1. Field of the Invention

This invention relates to copolymerizable blocked isocyanate diols useful in urethane condensation polymerization reactions. The invention also relates to a process for the preparation of such blocked isocyanate diols, and in a further aspect is directed to crosslinkable, linear polyurethanes of high molecular weight prepared employing the blocked isocyanate diols.

2. Description of the Prior Art

It is well known that condensation of an organic diisocyanate such as toluene diisocyanate with an organic polyol such as polypropylene glycol in the presence, as may be necessary, of other additives results in polyurethanes useful for various purposes.

In many fields of application, such as in manufacturing polyurethane films, foams, textiles, shaped articles, coating compounds and wire enamels, a one-package urethane composition is desired which is stable at room temperature, but reacts at elevated temperatures as if free isocyanate groups were present to form the desired polyurethane. Compositions of this type contain "blocked" isocyanates which are prepared by reacting an organic isocyanate with a blocking agent, which contains an active hydrogen atom, such as a phenol, an aliphatic or aromatic amine, etc. The isocyanate compound thus blocked has only limited thermal stability, generally dissociating at temperatures of 150° to 200° C., to regenerate the free isocyanate group, which can react further with, e.g., a polymer containing active hydrogen atoms to form an insoluble polymer. For example, U.S. Pat. No. 2,568,885 discloses the preparation of non-crosslinkable polyurethanes of high molecular weight by polymerizing blocked diisocyanates with difunctional compounds containing active hydrogens such as diols, diamines, aminoalcohols, and dicarboxylic acids. U.S. Pat. No. 3,833,525 teaches a one-package polyurethane system consisting of blocked diisocyanate, a polyol and a nitrogen-containing heterocyclic compound, in which system the isocyanate groups are liberated at a temperature as low as 70° C.

Blocked isocyanate groups may be used not only in preparing polyurethanes, but they may also be present in the final polymer to provide a means for crosslinking the polymer (see Saunders and Frisch, "Polyurethanes: Chemistry and Technology", Vol. XVI, Part II, New York: Interscience Publishers, 1962, pp. 489–490). Typically, crosslinkable, terminally blocked isocyanate polymers are prepared by reacting a polyisocyanate with a polyol or a hydroxy-terminated polymer to a low molecular weight using an excess of polyisocyanate to form an isocyanate terminated prepolymer, which is then reacted with a blocking agent.

The crosslinkable, terminally blocked polymers of the prior art are generally of low molecular weight, because if they were polymerized to a high molecular weight, they would contain very few terminally blocked isocyanate groups, thereby limiting their potential for crosslinking. Because of their low molecular weight, these polymers cannot be molded or shaped into useful films or articles before being crosslinked, so that their applicability is quite limited.

Japanese Pat. No. 70 34,708 discloses blocked isocyanate monomers containing an ethylenically unsaturated group which are polymerized to form thermosetting polyurethane resins of high molecular weight.

The present invention provides a blocked isocyanate diol which will copolymerize to form a linear, crosslinkable polyurethane of high molecular weight containing relatively many blocked isocyanate groups per polymer chain, which can be shaped into useful articles before being crosslinked.

SUMMARY OF THE INVENTION

The blocked isocyanate diol provided herein comprises an organic diisocyanate containing a blocked isocyanate group and an isocyanate group which has been reacted with the amine portion of an amine diol of one of the general formulae:

$$NH(DOH)_2 \text{ or } NHRD'(OH)_2$$

wherein

D is an alkylene ($C_2$–$C_{20}$) or aralkylene ($C_7$–$C_{20}$) radical in which the hydroxyl group is attached to an aliphatic carbon atom, D′ is an alkylene ($C_2$–$C_{20}$) or aralkylene ($C_8$–$C_{20}$) radical in which each of the hydroxyl groups is attached to a different aliphatic carbon atom, and R is hydrogen or an unsubstituted or substituted alkyl, alkenyl cycloalkenyl, cycloalkylene, aryl, alkaryl, or aralkyl radical which is not reactive with active hydrogen atoms or isocyanate groups.

The novel blocked isocyanate diols herein may be copolymerized to form one-package, stable polyurethane compositions which are crosslinkable with heat. The lability of the blocking groups upon application of moderate heat enables the liberated isocyanate groups to copolymerize, crosslink, or react with a substrate containing active hydrogen, as desired. The thermoplastic polyurethanes of high molecular weight thus prepared have a distinct advantage over the crosslinkable polyurethanes of the prior art in that the former can be shaped into articles or made into films before being crosslinked and thereby insolubilized. These polyurethanes find use in a wide variety of applications such as, for example, in textiles and paper.

DESCRIPTION OF THE PREFERRED EMBODIMENTS

The copolymerizable blocked isocyanate diols herein may be readily prepared according to the following representative reaction sequence (using methyl ethyl ketoxime as the blocking agent, toluene diisocyanate as the organic diisocyanate, and diethanolamine as the amine diol):

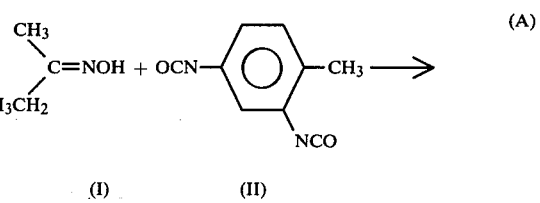

(A)

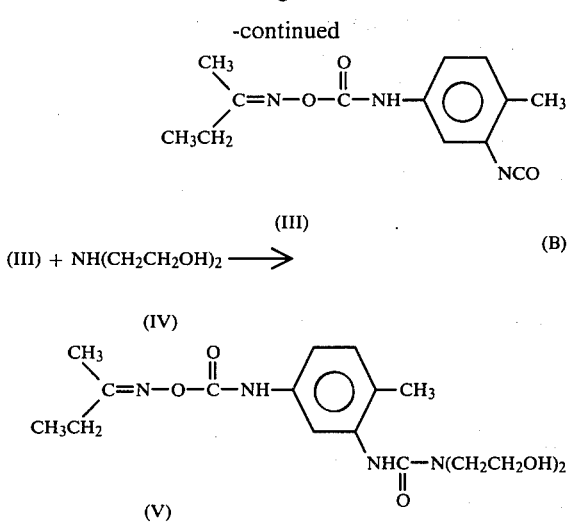

(III) + NH(CH₂CH₂OH)₂ ⟶ (B)

In step (A), a blocking agent (I) is reacted with an organic diisocyanate (II) to produce a blocked adduct (III), which is then reacted in a second step (B) with an amine diol (IV) to produce the blocked isocyanate diol (V). The practitioner will recognize that when the diisocyanate employed comprises an isomeric mixture, e.g., a mixture of 2,4- and 2,6-toluene diisocyanate, the final product will likewise be comprised of an isomeric mixture. Similarly, diisocyanates which have isocyanate groups of nearly equal reactivity will result in a mixture of products, with the desired product being isolated from the mixture by suitable techniques.

It is noted that the above reaction sequence may be reversed, but a product mixture containing unwanted by-products will be obtained because of the high reactivity of the amine diol. The low yield of blocked isocyanate diol obtained thereby makes this reverse sequence undesirable from a commercial standpoint.

The blocking agents which are applicable herein are compounds which contain an active hydrogen atom reactive with the isocyanate group and which will at moderate temperatures (up to 200° C.) cleave from the blocked adduct, liberating free isocyanate. The reactive hydrogen atoms are commonly attached to oxygen (e.g., hydroxyl groups), sulfur, or nitrogen atoms, however; they may also be attached to carbon atoms which are highly activated by other groups in close proximity therewith. Suitable blocking agents include, for example, ethyl malonate, acetylacetone, ethyl acetoacetate, 1-phenyl-3-methyl-5-pyrazolone, hydroxylamine, thiophenol, caprolactam, pyrocatechol, propyl mercaptan, N-methyl aniline, diphenyl amine, phenol, 2,4-diisobutylphenol, methyl ethyl ketoxime, α-pyrrolidone, t-butyl alcohol, ethylene imine, propylene imine, and the like. The preferred blocking agents herein are those containing a hydroxyl group, and in particular, methyl ethyl ketoxime, t-butyl alcohol and phenol because of their relative ease of reaction and the low temperatures at which they become unblocked.

Any organic diisocyanate compounds such as aliphatic, aromatic or cycloaliphatic diisocyanates which will react with polyhydric compounds to form polyurethane prepolymers are applicable herein. Representative of the types of organic diisocyanates (or mixtures thereof) which may be employed in the present process are ethylene diisocyanate, ethylidene diisocyanate, propylene-1,2-diisocyanate, cyclohexylene diisocyanate, meta-phenylene diisocyanate, 2,4-toluene diisocyanate, 2,6-toluene diisocyanate, 3,3'-dimethyl-4,4'-biphenylene diisocyanate, 3,3'-dimethoxy-4,4'-biphenylene diisocyanate, 3,3'-diphenyl-4,4'-biphenylene diisocyanate, 3,3'-dichloro-4,4'-biphenylene diisocyanate, 1,5-naphthalene diisocyanate, furfurylidene diisocyanate, 1,3-xylylene diisocyanate, 1,4-xylylene diisocyanate, 4,4'-biphenylene diisocyanate, hexamethylene diisocyanate, 4,4'-methylene-bis-phenyl diisocyanate, 4,4'-methylene-bis-cyclohexyl diisocyanate, 3-isocyanatomethyl-3,5,5-trimethyl cyclohexyl isocyanate (isophorone diisocyanate), and the like. The preferred diisocyanates to be used herein are those in which the isocyanate groups are of different reactivity such that the blocking agent will react predominantly with the more reactive isocyanate group. Use of these preferred diisocyanates will enable each isocyanate group to react independently of the other, thereby enhancing the yield of the desired product, while at the same time minimizing formation of side products. The diisocyanate compounds which are particularly preferred are isophorone diisocyanate and toluene diisocyanate, such as HYLENE TM (Registered Trademark of DuPont de Nemours, Inc.).

In the first step for preparing the blocked isocyanate diols herein, the organic diisocyanate and blocking agent are admixed under anhydrous conditions and generally in an inert atmosphere such as under gaseous nitrogen. The relative amounts of reagents used can be expressed in terms of an optimum stoichiometric molar ratio of 1.0:1.0, but nevertheless, the ratio of blocking agent to diisocyanate may range from about 0.8:1.0 to 1.2:1.0. The reaction may be run in bulk (i.e., without solvent) or in an organic solvent which is dry and inert to isocyanate groups, amino groups, hydroxyl groups, and the active hydrogen of the blocking agent. Typical such solvents include, e.g., toluene, methylene chloride, ethyl acetate, acetone, methyl ethyl ketone, and the like. Catalysts commonly used in urethane reactions may be employed in this first step and include tin compounds such as stannous octanoate and dibutyl tin laurate, iron naphthenoate, antimony octanoate, lead octanoate, tertiary amines, and the like. The particular catalyst used, if any, is not important in the present process. It will be noted that these same catalysts may also be used as polymerization catalysts and as unblocking catalysts for the copolymer prepared from the amine diol, as described hereinbelow.

Depending on the reagents employed, the starting materials may be added simultaneously to the reaction vessel, or it may be necessary to add one of the reagents slowly to the other at an elevated temperature. After all ingredients have been added, the mixture is reacted, with stirring, at a temperature and for a period of time which depends, inter alia, on the diisocyanate employed. Thus, for aromatic diisocyanates the reaction is carried out at about 25° to 100° C. for about 1 to 8 hours, preferably 35°–60° C. for 1.5–5 hours; while for aliphatic diisocyanates the reaction proceeds at about 50° to 120° C. for about 3–10 hours, preferably 80°–100° C. for 5–7 hours. The degree of conversion of the reactants to the blocked adduct can be determined by analysis of the amount of unreacted isocyanate groups present in the reaction mixture, which theoretically should be half the original amount present, if the reaction proceeds to 100% completion. This amount may sometimes be less than half if moisture is present to block some of the free isocyanate groups. The reaction product is commonly obtained in the form of a viscous liquid, which may be isolated, diluted with solvent, and added to the amine diol for further reaction. Alternatively, the amine diol can be added directly to the reaction mixture with no isolation of the intermediate product.

The amine diol used in the second step of the process has one of the two formulae specified hereinabove. Examples of typical amine diols falling within these formulae are diethanolamine, diisopropanolamine, aminopropyl diethanolamine, 2-amino-2-methyl-1,3-propanediol, 2-amino-2-ethyl-1,3-propanediol, and the like. In accordance with the process herein, the amine diol is admixed with the blocked adduct in a molar ratio of blocked adduct to amine diol of from about 0.8:1.0 to 1.1:1.0, the optimum ratio being 1.0:1.0. The addition of the two compounds together and the reaction itself are generally conducted under an inert atmosphere at a temperature of about 0° to 100° C., preferably 10°–40° C., for a total time, depending on the temperature and nature of the reagents, of about 1–8 hours, preferably 2–4 hours. Catalysts such as those described above for the first reaction may be utilized, but preferably no catalyst is employed. The use of low temperatures and no catalyst favors the desired reaction of the remaining free isocyanate group with the amine functionality rather than with the hydroxyl groups of the amine diol. The reaction may be carried out in bulk, but is preferably carried out in an inert organic solvent such as those described above. The product is generally quite soluble in these solvents. The progress of the reaction can be monitored by means of infrared spectroscopy with respect to the disappearance of the characteristic absorption band exhibited by the free isocyanate group. Upon completion of the reaction, any solvent present may be removed from the system if the solvent is not to be used in the subsequent polymerization step. However, the blocked diol may remain in solution form if it is to be copolymerized by means of a solution technique.

The blocked diols are particularly suited herein for use in urethane condensation reactions in the preparation of copolymers. The diol may be reacted, for example, with a polyester diol and a diisocyanate, or may be used to chain-extend isocyanate-terminated prepolymers under conditions used for known chain-extenders such as polyols of low molecular weight. In any case, at least about 1% by weight of the polyurethane which results from the polymerization should be derived from the blocked isocyanate diol to obtain satisfactory crosslinking systems.

When the above-described diols are used in the preparation of copolymers, there may be employed any of the usual polymerization methods which are well known to those skilled in the art and which are particularly suited for the copolymer to be prepared. Thus, such copolymers may be produced by means of processes utilizing solution or bulk polymerization or nonaqueous suspension or emulsion polymerization techniques. The polymerization reaction is preferably carried out under nitrogen using moisture-free conditions.

The blocked isocyanate diol may be copolymerized with a copolymerizable comonomer using heat alone or using heat in conjunction with an additive. The temperature used for polymerization depends on several factors, for example, on the blocking agent, the diisocyanate, and the type of polymerization catalyst used, e.g., dibutyltin dilaurate and triethylenediamine, but ordinarily ranges from 50° to 100° C. The reaction time similarly varies, but must be sufficient in all cases to provide a molecular weight of at least 15,000, and preferably at least 20,000. This high molecular weight allows the polyurethanes herein to be shaped into articles or made into films before they are crosslinked.

Self-crosslinking of the polymers herein is initiated by the application of heat to a dried film of the polymer at a temperature and for a time period which depend on the particular polymer employed, sufficient to liberate (unblock) the blocked isocyanate group, thereby rendering the film insoluble in a solvent such as tetrahydrofuran. Typically, heating at 50°–150° C. for 20–30 minutes is adequate for this purpose. More reactive polymers, e.g., those containing catalysts for unblocking the isocyanate group, may crosslink at temperatures as low as room temperature when stored for a certain length of time. Initiation of crosslinking of the polymer may be assisted, if desired, by adding a small quantity of a conventional crosslinking agent thereto and then applying heat, if necessary, to unblock the blocked isocyanate group. Illustrative of suitable crosslinking agents are the polyalkanol amines such as triethanolamine, tetrakis (2-hydroxypropyl)ethylene diamine, 1,4-bis-(2-hydroxypropyl)2-methylpiperazine, 1,2,4-trimethylpiperazine, glycerol, ethylene glycol, diethylene glycol, triethylene glycol, triethylene tetramine, tetraethylene pentamine, methane diamine, and the like. In general, applicable crosslinking agents herein may be defined as compounds containing at least two functional groups which will react with the liberated isocyanate group of the polymer. The crosslinking agent is ordinarily added to the polymer in proportions of about 20–200%, based on the weight of the blocked diol.

It is to be noted that the unblocking of the isocyanate group and the subsequent crosslinking of the copolymer may be catalyzed (i.e., more crosslinking will take place in a given period of time at a given temperature, or alternatively, shorter time periods or lower temperatures will result in a comparable degree of crosslinking) with the use of common urethane catalysts, such as dibutyl tin dilaurate, iron naphthenoate, stannous octanoate, antimony octanoate, lead octanoate, and tertiary amines such as triethylene diamine, trialkanolamines, and N-methyl diethanolamine. The addition of such unblocking catalysts to the crosslinkable polymer system in concentrations of about 0.1 to 10%, based on the weight of the polymer, provides a means of obtaining a significantly improved degree of crosslinking as compared with uncatalyzed crosslinking systems. The higher levels of catalyst within the above-specified range are more suitable when tertiary amines are employed as the catalyst. As an alternative to adding the catalyst to the prepared polymer, the catalyst may also be incorporated as a comonomer in the polyurethane, in the same amounts as above, whereby catalytic activity will be similarly enhanced.

The following examples illustrate further the embodiments of the present process. In these examples, all parts and percentages are given by weight and all temperatures in degrees Celsius unless otherwise noted.

EXAMPLE I

This example illustrates the preparation of a blocked isocyanate diol in accordance with the present process.

To a flask equipped with stirrer, condenser, thermometer, gas-inlet tube and slow-addition tube was added 871.0 g. of toluene diisocyanate (an 80:20 mixture of the 2,4- and 2,6-diisocyanate isomers). The temperature was then raised to 40° C., and 435.0 g. of methyl ethyl ketoxime was added slowly over a period of 2.25 hours, with the temperature ranging between 40° and 45° C. This temperature was maintained under a slow stream of nitrogen for an additional 1.5 hours, after which time the reaction mixture was cooled and discharged from the reaction flask. The reaction product (the blocked adduct) was a viscous liquid having 15.3% residual isocyanate groups versus 16.1% theoretical.

Another flask was set up, equipped as in the preceding synthesis, but having two slow-addition tubes attached thereto. The first slow-addition tube was charged with 103.5 g. of diethanolamine, while the second tube was charged with 261.2 g. of the blocked adduct above and 90.0 g. of dry acetone. A slow stream of nitrogen was led into the reaction flask and agitation initiated. The contents of the two slow-addition tubes were then added simultaneously over a period of three hours, while the temperature was maintained between 18° and 28° C. After slow addition was complete, the reaction was allowed to continue for an additional 1.5 hours, after which the product, which was a viscous liquid of 80% concentration in acetone, was poured from the reaction flask. Infrared spectroscopy indicated complete absence of the isocyanate functionality, and further analysis revealed the presence of 1.14% unreacted amine diol. A dried sample of the product had a melting point of 53° to 60° C.

EXAMPLE II

To a flask equipped as in Example I was added 63.3 g of diisopropanolamine. The slow-addition tube was charged with 130.6 g. of the blocked adduct of Example I and 48.8 g. of dry acetone. Stirring was begun and the temperature of the reaction reduced to 12° C. The solution of the blocked adduct in acetone was added to the flask over a period of 1.75 hours at 12° C. The reaction was continued for an additional one hour, after which time the reaction mixture was poured from the flask. The product, which was a viscous liquid, was found by ir analysis to have no isocyanate groups. Further analysis indicated the presence of 7.2% by weight of the original diisopropanolamine. A dried sample of the product had a melting point of 72°-82° C.

EXAMPLE III

To a reaction flask equipped as in Example I was added 71.0 g. of 2-amino-2-methyl-1,3-propanediol, 61.8 g, of dry acetone and 36.0 g. of dry toluene. A solution of 179.0 g. of the blocked adduct of Example I and 10.0 g. of dry acetone was added through a slow-addition tube to the reaction mixture at room temperature (20°-25° C.) over a period of 3 hours, and a nitrogen atmosphere was maintained throughout the reaction. After this time the product was discharged from the reactor as an opaque viscous liquid. Ir analysis revealed no remaining isocyanate groups, and further analysis showed 4.0% residual amine diol. A dried sample of the product had a broad melting point of 67°-75° C.

EXAMPLE IV

To a reaction flask equipped as in Example I was added 88.1 g. of 2-amino-2-ethyl-1,3-propanediol and 70.6 g. of dry acetone. A solution of 195.8 g. of the blocked adduct of Example I and 10.0 g. of dry acetone was then added to the reaction mixture over a period of two hours. The temperature was allowed to rise from about 22° C. to 33° C. The reaction was continued for an additional one hour at 30° C. under a nitrogen atmosphere, and the mixture then discharged from the reactor. The product, a clear viscous liquid, was formed by ir spectroscopy to have no observable isocyanate groups. Further analysis revealed a residual amine diol content of 1.67% and a melting point of 77°-87° C.

EXAMPLE V

To a reaction flask equipped as in Example I was added 222.3 g. of 3-isocyanatomethyl-3,5,5-trimethyl cyclohexyl isocyanate (isophorone diisocyanate) and 74.12 g. of tertiary-butyl alcohol. The temperature was raised to 90° C. and was maintained for 6 hours. A slow stream of nitrogen into the vessel was maintained throughout the reaction. After the six-hour reaction period, the reaction mixture was cooled to room temperature to yield a viscous liquid having 17.0% residual isocyanate versus 14.2% theoretical. The adduct was not isolated from the reaction mixture.

A total of 100 g. of dry acetone was added to the cooled reaction mixture. Then 126.14 g. of diethanolamine was added to the reaction mixture at room temperature over a period of 2 hours. A cold-water bath was applied to the reaction flask to maintain the low temperature because of the exothermic nature of the reaction. After slow-addition was complete, the reaction was allowed to continue for an additional hour until infrared analysis indicated the complete absence of isocyanate groups. The reaction mixture, which consisted of a pale-yellow, viscous solution of the product in acetone, was poured from the reaction flask. A dried sample of the product melted at 75°-80° C.

EXAMPLE VI

To a flask equipped as in Example I was added 94.11 g. of phenol and 222.3 g. of isophorone diisocyanate. The reaction was heated to 90° C. and held at that temperature for 5 hours. The reaction mixture was then cooled to room temperature and 100 g. of dry acetone was added thereto. A total of 105.14 g. of diethanolamine were then slowly added over a period of 0.5 hour while the reaction mixture was maintained at room temperature. The reaction was allowed to continue for an additional hour, after which the reaction mixture was poured from the reaction flask. A dried sample of the product had a melting point of 63°-68° C.

EXAMPLE VII-X

These examples illustrate the preparation of the self-crosslinking polyurethanes of high molecular weight in accordance with the procedures outlined herein.

Four polymers were prepared as follows:

The initial ingredients listed under A in Table I were added in the given amounts to a reactor equipped as in Example I. The ingredients were stirred and a stream of dry nitrogen gas allowed to flow through the reactor. The temperature was then raised to the specified addition temperature, at which temperature the given amount of toluene diisocyanate (80/20 mixture of 2,4/2,6-isomers) was added uniformly over the indicated addition period. The reaction was allowed to continue at the specified temperature for the given reaction time. A noticeable increase in viscosity of the reaction mixture was observed during each reaction. At the end of the reaction period, the indicated solvents were added in the given amounts to the reaction mixture, which was thereafter cooled and poured from the reactor.

Each of the polyurethane solutions thus obtained was analyzed, and the properties summarized in Table II.

The intrinsic viscosity was determined according to the procedure described in ASTM Standards (D1795)21.

A dried film of each of the polymers was completely soluble in tetrahydrofuran (THF), however, when heated for 20 minutes at 130° C., each film became insoluble in THF, indicating that the heating effectively unblocks the isocyanate group, which can then crosslink, thereby insolubilizing the polymer.

TABLE I

| | Examples | | | |
|---|---|---|---|---|
| | VII | VIII | IX | X |
| A. Initial Ingredients (g.): | | | | |
| Blocked diol of Example I (80% solution in acetone) | 83.5 | — | — | — |
| Blocked diol of Example II (80% solution in acetone) | — | 48.5 | — | — |
| Blocked diol of Example III (69.8% solution in acetone) | — | — | 52.4 | — |
| Blocked diol of Example IV (73.3% solution in acetone) | — | — | — | 51.8 |
| A diethylene glycol/adipic acid polyester diol of about 115 hydroxyl number | 399.0 | 399.0 | 399.0 | 399.0 |
| Acetone | 139.0 | — | — | — |
| Toluene | — | 222.0 | 222.0 | 222.0 |
| Ethyl acetate | — | 148.0 | 148.0 | 148.0 |
| Dibutyl tin dilaurate | 0.15 | 0.15 | 0.15 | 0.15 |
| B. Addition of Toluene Diisocyanate: | | | | |
| Amount of Diisocyanate (g.) | 83.5 | 91.0 | 91.0 | 91.0 |
| Addition temperature (°C.) | 56–58 | 50 | 50 | 50 |
| Addition period (hours) | 1.67 | 2 | 0.67 | 2 |
| C. Reaction Conditions: | | | | |
| Reaction temperature (°C.) | 56–58 | 80 | 80 | 80 |
| Reaction time (hours) | 3.67 | 6.5 | 9.5 | 6.75 |
| D. Solvents (g.): | | | | |
| Acetone | 215.0 | — | 100.0 | 100.0 |
| Toluene | — | 232.0 | 232.0 | — |
| Ethyl acetate | — | 232.0 | 232.0 | 364.0 |
| Methyl alcohol | — | 3.5 | 3.5 | 3.5 |

TABLE II

| Example | Percent Solids | Intrinsic Viscosity in THF (dl./g.) | Viscosity (cps.) |
|---|---|---|---|
| VII | 58.7 | 0.37 | 9100 |
| VIII | 39.2 | 0.32 | 6000 |
| IX | 37.3 | 0.38 | 47,000 |
| X | 39.9 | 0.46 | 24,000 |

EXAMPLE XI

This example illustrates the preparation of a self-catalyzed, self crosslinking polyurethane aqueous dispersion from the blocked isocyanate diols herein.

To a reactor equipped as in Example I were added 387.8 g. of a diethylene glycol/adipic acid polyester diol of approximately 115 hydroxyl number, 17.5 g. of diethylene glycol, 39.2 g. of N-methyl diethanolamine, 80.2 g. of the blocked isocyanate diol of Example I, 728.0 g. of acetone, and 0.18 g. of dibutyl tin dilaurate.

These ingredients were stirred and brought to reflux at 56° C. Then, 179.6 g. of the toluene diisocyanate (80:20 isomer) described above was added over a period of one hour. After addition was complete, the mixture was heated for an additional 3 hours. At the end of the reaction, 7.9 g. of Surfactol 365 (a registered trademark for a surface active agent available from Baker Chemical Co.) was added, and then, a mixture of 815.0 g. water, 39.9 g. of glacial acetic acid, and 6.1 g. of Surfactol 365 was added over a period of 0.5 hours.

After the addition was complete, a distillation head was attached to the reactor and the acetone in the mixture was distilled off. During the distillation the reaction mixture changed from a solution to a milky, aqueous dispersion. After most of the acetone was removed, as indicated by the beginning of an increase in the distillation temperature, the reaction mixture was cooled and poured from the reactor. The polyurethane dispersion thus formed was found to have the following properties:

| Percent Solids: | 38.2% |
|---|---|
| Intrinsic viscosity in THF: | 0.24 dl./g. |
| pH: | 4.7 |
| Particle size: | <0.11 microns |
| Viscosity: | 480 cps. |

Unheated dried films of the polymer product were found to be soluble in THF, but when the film was aged for one month at room temperature, it became insoluble. Similarly, when the film was heated at 60° C. and at 130° C. for 20 minutes each, it was found to be insoluble in THF. It can be seen from these results that the polymer herein, which is prepared using a tertiary amine, a catalyst for unblocking the isocyanate group, cures by aging or under very mild conditions of heat.

EXAMPLE XII

This example illustrates the chain-extending properties of the blocked isocyanate diols herein.

An isocyanate-terminated prepolymer was prepared by reacting 861.0 g. of a mixture of polyether diols having an average molecular weight of about 650 with 554.0 g. methylene-bis-phenyl diisocyanate. The resulting prepolymer, which had a residual NCO content of 2.25%, was chain-extended with the blocked diols of Examples V and VI and with 1,6-hexane diol (as a comparison) in the amounts given in Table III.

TABLE III

| | Polymer | | |
|---|---|---|---|
| Ingredients (g.) | A | B | C |
| Polyurethane prepolymer | 81.2 | 81.2 | 81.2 |
| Toluene | 50 | 50 | 50 |
| Dry acetone | 25 | 25 | 25 |
| Blocked diol of Example V (80% solution in acetone) | 23.9 | — | — |
| Blocked diol of Example VI (80% solution in acetone) | — | 24.8 | — |
| 1,6-hexane diol (comparative) | — | — | 5.6 |

The above ingredients were mixed in a jar and allowed to react overnight at room temperature under agitation. The solutions increased considerably in viscosity, and films cast from the solutions were moderately tough and flexible, as compared with the soft and tacky films obtained from solutions of the polyurethane prepolymer alone. Films of all three polymers were soluble in THF before heating thereof, but when heated at 130° C. for 30 minutes, the films of Polymers A and B were found to be insoluble in THF, while the heated film of Polymer C remained soluble. The insolubility of Polymers A and B, after heating, is evidence of the unblocking of the isocyanate group of the blocked diol, and subsequent reaction to crosslink the polymers.

Summarizing, a blocked isocyanate diol is provided which readily copolymerizes to form thermoplastic polyurethanes of high molecular weight which are crosslinkable upon application of heat thereto.

Now that the preferred embodiments of the present invention have been described in detail, various modifications and improvements thereon will become readily apparent to the practitioner. Therefore, the spirit and scope of the invention are to be limited only by the appended claims, and not by the foregoing specification.

What is claimed is:

1. A blocked isocyanate diol consisting of an organic diisocyanate containing one isocyanate group which has been reacted with a blocking agent containing a hydroxyl group, and a second isocyanate group which has been reacted with the amine portion of an amine diol of one of the general formulae:

$NH(DOH)_2$ or $NHRD'(OH)_2$ wherein
D is an alkylene ($C_2$–$C_{20}$) or aralkylene ($C_7$–$C_{20}$) radical in which the hydroxyl group is attached to an aliphatic carbon atom,
D' is an alkylene ($C_2$–$C_{20}$) or aralkylene ($C_8$–$C_{20}$) radical in which each of the hydroxyl groups is attached to a different aliphatic carbon atom, and
R is hydrogen or an unsubstituted or substituted alkyl, alkenyl, cycloalkyl, cycloalkenyl, aryl, alkaryl, or aralkyl radical which is not reactive with active hydrogen atoms or isocyanate groups.

2. Claim 1 wherein said blocking agent is methyl ethyl ketoxime.

3. Claim 1 wherein said amine diol is selected from the group consisting of diethanolamine, diisopropanolamine, 2-amino-2-methyl-1,3-propanediol, and 2-amino-2-ethyl-1,3-propanediol, and wherein said organic diisocyanate is toluene diisocyanate or isophorone diisocyanate.

4. claim 1 wherein said blocking agent is t-butyl alcohol or phenol.

5. A process for preparing a blocked isocyanate diol comprising the steps of:
  a. reacting a blocking agent which contains a hydroxyl group with an organic diisocyanate at a temperature of 25°–100° C. for 1–8 hours for aromatic diisocyanates and at 50°–120° C. for 3–10 hours for aliphatic diisocyanates, wherein the ratio of blocking agent to diisocyanate is from 0.8:1.0 to 1.2:1.0, to obtain a blocked adduct;
  b. reacting the blocked adduct with an amine diol of one of the general formulae:

$NH(DOH)_2$ or $NHRD'(OH)_2$ wherein
D is an alkylene ($C_2$–$C_{20}$) or aralkylene ($C_7$–$C_{20}$) radical in which the hydroxyl group is attached to an aliphatic carbon atom,
D' is an alkylene ($C_2$–$C_{20}$) or aralkylene ($C_8$–$C_{20}$) radical in which each of the hydroxyl groups is attached to a different aliphatic carbon atom, and
R is hydrogen or an unsubstituted or substituted alkyl, alkenyl, cycloalkyl, cycloalkenyl aryl, alkaryl, or aralkyl radical which is not reactive with active hydrogen atoms or isocyanate groups,
wherein the ratio of blocked adduct to amine diol is from 0.8:1.0 to 1.1:1.0, said reaction being carried out at a temperature of 0°–100° C. for 1–8 hours under anhydrous conditions; and
  c. isolating the resultant product.

6. claim 5 wherein said organic diisocyanate is aromatic and step (a) is carried out at 35°–60° C. for 1.5–5 hours.

7. claim 6 wherein said organic diisocyanate is aliphatic and step (a) is carried out at 80°–100° C. for 5–7 hours.

* * * * *